US010492786B2

United States Patent
Marczyk et al.

(10) Patent No.: US 10,492,786 B2
(45) Date of Patent: Dec. 3, 2019

(54) PAIR OF DOUBLE STAPLE PUSHER IN TRIPLE ROW STAPLER

(71) Applicant: Covidien LP, Mansfield, MA (US)

(72) Inventors: Stanislaw Marczyk, Stratford, CT (US); Lee Olson, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 235 days.

(21) Appl. No.: 15/688,272

(22) Filed: Aug. 28, 2017

(65) Prior Publication Data

US 2017/0354414 A1    Dec. 14, 2017

Related U.S. Application Data

(63) Continuation of application No. 15/338,796, filed on Oct. 31, 2016, now Pat. No. 9,743,930, which is a continuation of application No. 13/945,564, filed on Jul. 18, 2013, now Pat. No. 9,498,213, which is a continuation of application No. 12/895,948, filed on Oct. 1, 2010, now Pat. No. 8,496,154.

(60) Provisional application No. 61/249,637, filed on Oct. 8, 2009.

(51) Int. Cl.
| | | |
|---|---|---|
| *A61B 17/072* | (2006.01) | |
| *A61B 17/115* | (2006.01) | |
| *A61B 17/064* | (2006.01) | |
| *A61B 17/068* | (2006.01) | |

(52) U.S. Cl.
CPC ...... *A61B 17/07207* (2013.01); *A61B 17/068* (2013.01); *A61B 17/0644* (2013.01); *A61B 17/115* (2013.01); *A61B 17/0682* (2013.01); *A61B 17/072* (2013.01); *A61B 2017/07214* (2013.01); *A61B 2017/07228* (2013.01); *A61B 2017/07242* (2013.01); *A61B 2017/07264* (2013.01); *A61B 2017/07278* (2013.01)

(58) Field of Classification Search
CPC ............. A61B 17/068; A61B 17/0682; A61B 17/0644; A61B 17/07207; A61B 17/115; A61B 2017/07214; A61B 2017/07271; A61B 2017/07285; A61B 2017/07278; A61B 2017/07242; A61B 2017/07262; A61B 2017/07235
USPC ....... 606/139, 213, 219, 153; 227/19, 175.1, 227/175.2, 176.1, 180.1
See application file for complete search history.

(56) References Cited

U.S. PATENT DOCUMENTS

| | | |
|---|---|---|
| D278,081 S | 3/1985 | Green |
| 4,715,520 A | 12/1987 | Roehr, Jr. et al. |
| 4,955,959 A | 9/1990 | Tompkins et al. |

(Continued)

FOREIGN PATENT DOCUMENTS

CN    101502429 A    8/2009

OTHER PUBLICATIONS

European Search Report No. 10251755 dated Jun. 25, 2014.

(Continued)

*Primary Examiner* — Scott A Smith
(74) *Attorney, Agent, or Firm* — Carter, DeLuca & Farrell LLP

(57) ABSTRACT

A staple cartridge includes outer and inner rows of retention slots that are adapted and configured to retain staples. The staple cartridge further includes a staple pusher including a plurality of pusher plates. A staple pusher includes pusher plates that are laterally spaced apart to engage staples within the outer rows of at least three rows of retention slots.

12 Claims, 8 Drawing Sheets

(56) References Cited

U.S. PATENT DOCUMENTS

| | | | |
|---|---|---|---|
| 4,978,049 | A | 12/1990 | Green |
| 5,395,034 | A | 3/1995 | Allen et al. |
| 5,415,334 | A | 5/1995 | Williamson et al. |
| 5,630,541 | A | 5/1997 | Williamson, IV et al. |
| 5,662,258 | A | 9/1997 | Knodel et al. |
| 6,131,789 | A | 10/2000 | Schulze et al. |
| 6,669,073 | B2 | 12/2003 | Milliman et al. |
| 7,635,074 | B2 | 12/2009 | Olson et al. |
| 7,641,091 | B2 | 1/2010 | Olson et al. |
| 7,673,781 | B2 | 3/2010 | Swayze et al. |
| 7,866,528 | B2 | 1/2011 | Olson et al. |
| 7,934,630 | B2 | 5/2011 | Shelton, IV et al. |
| 7,997,469 | B2 | 8/2011 | Olson et al. |
| 8,127,975 | B2 | 3/2012 | Olson et al. |
| 8,336,753 | B2 | 12/2012 | Olson et al. |
| 8,496,154 | B2 | 7/2013 | Marczyk et al. |
| 9,498,213 | B2 | 11/2016 | Marczyk et al. |
| 9,743,930 | B2 * | 8/2017 | Marczyk .......... A61B 17/07207 |
| 2007/0075115 | A1 | 4/2007 | Olson et al. |
| 2007/0194079 | A1 | 8/2007 | Hueil et al. |
| 2008/0023522 | A1 | 1/2008 | Olson et al. |

OTHER PUBLICATIONS

Canadian Office Action for application No. 2,717,114 dated Jun. 2, 2016.
Chinese Office Action dated Apr. 13, 2018 issued in corresponding Chinese Appln. No. 2016106701146.
Chinese Office Action dated Nov. 5, 2018 issued in corresponding CN Appln. No. 201610670114.6.
European Examination Report dated May 14, 2019 issued in corresponding EP Appln. No. 10 251 755.4.

\* cited by examiner

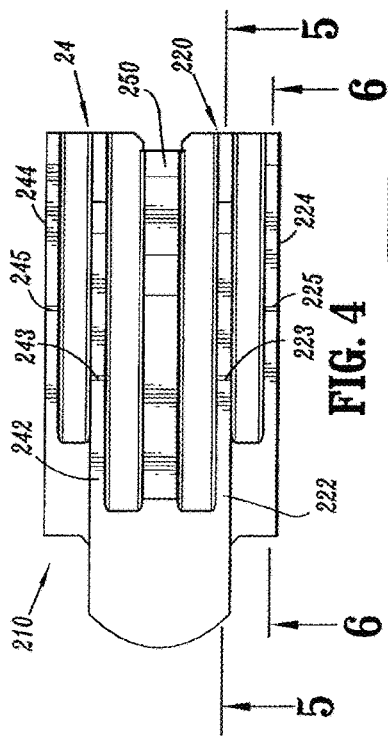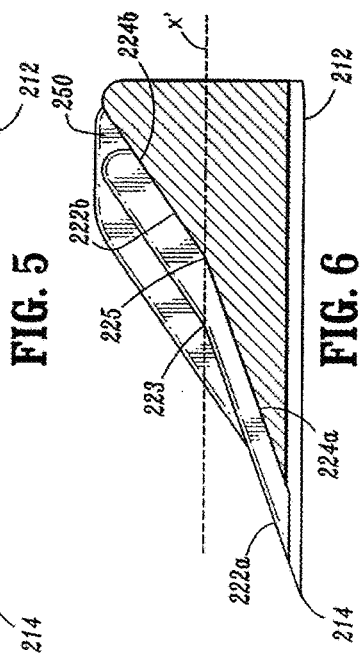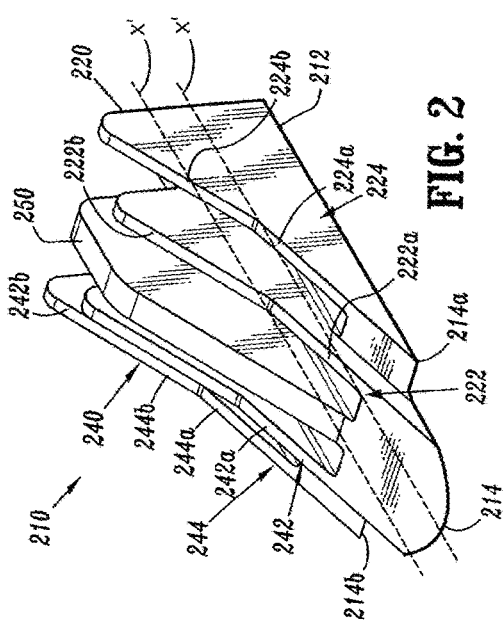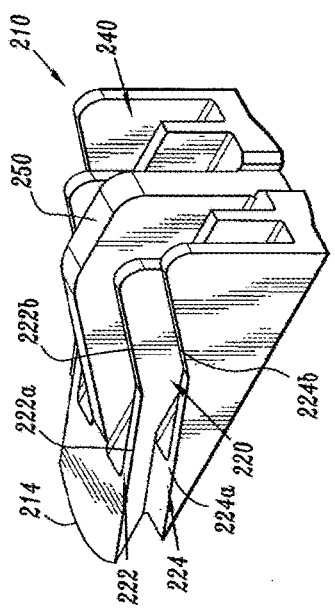

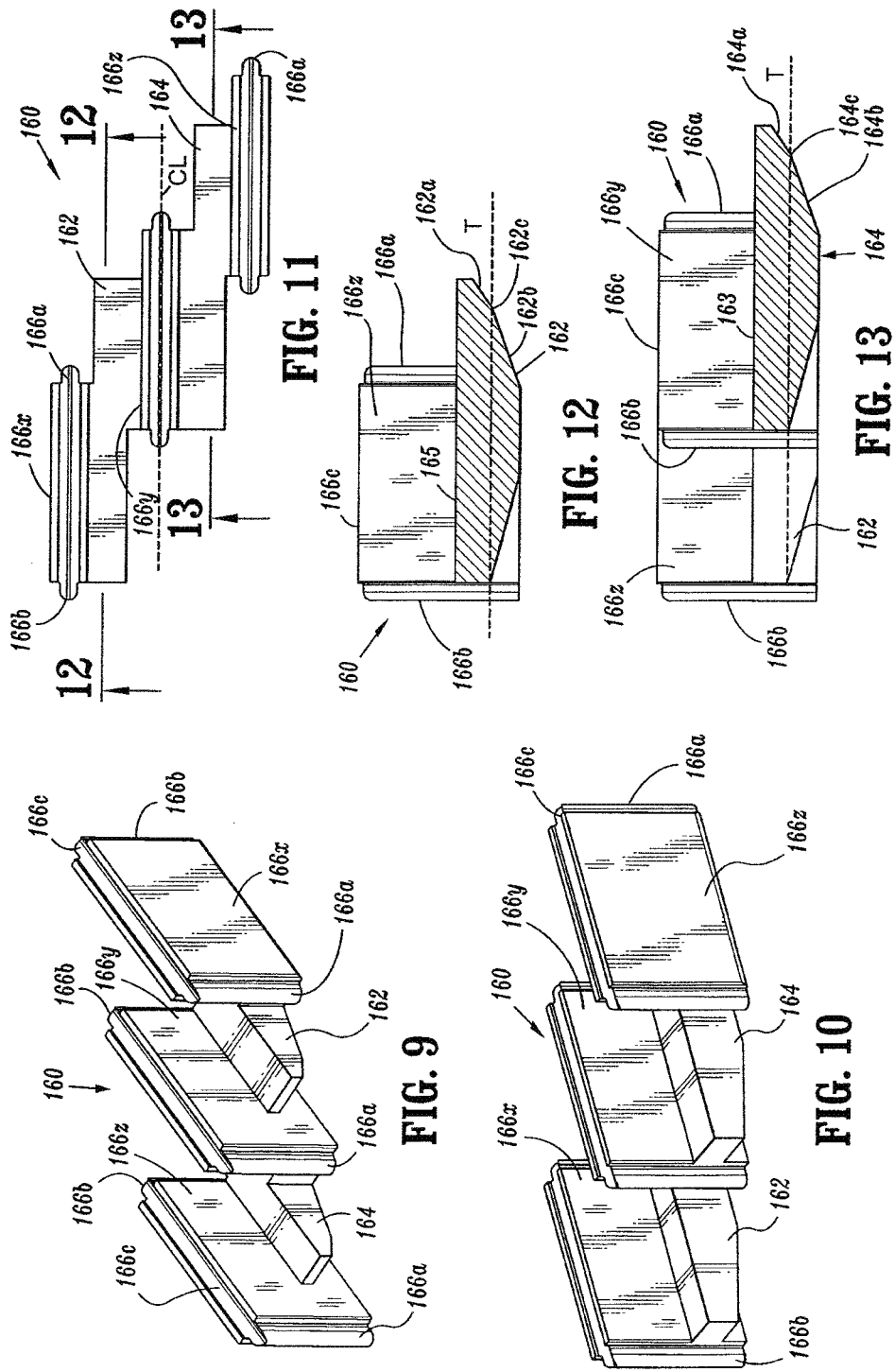

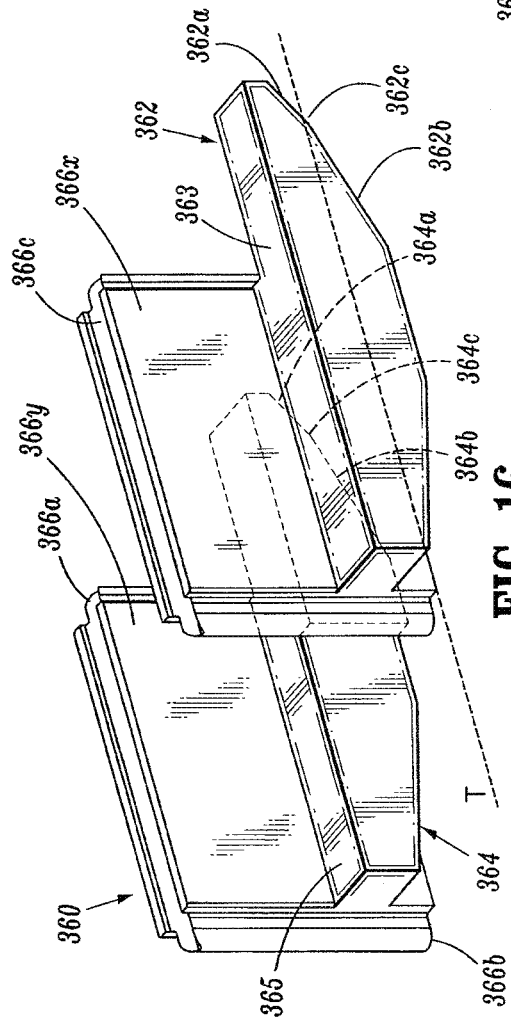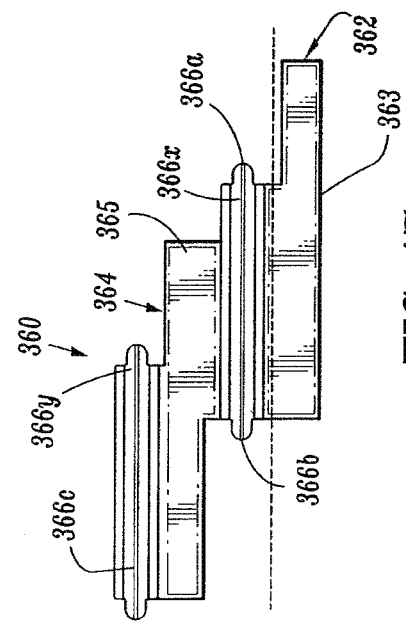

PAIR OF DOUBLE STAPLE PUSHER IN TRIPLE ROW STAPLER

CROSS REFERENCE TO RELATED APPLICATIONS

This application is a continuation of U.S. patent application Ser. No. 15/338,796, filed Oct. 31, 2016, which is a continuation of U.S. patent application Ser. No. 13/945,564, filed Jul. 18, 2013, (now U.S. Pat. No. 9,498,213), which is a continuation of U.S. patent application Ser. No. 12/895,948, filed Oct. 1, 2010, (now U.S. Pat. No. 8,496,154) which claims priority to, and benefit of, U.S. Provisional Application Ser. No. 61/249,637, filed Oct. 8, 2009, the disclosure of which is hereby incorporated by reference in its entirety.

BACKGROUND

Technical Field

The present disclosure is related to a stapling apparatus and, more particularly, to a staple drive assembly for use in a staple cartridge of a stapling apparatus.

Background of Related Art

Surgical stapling devices are widely used in surgical procedures to fasten body tissue quickly and efficiently by driving fasteners or staplers into the tissue. In certain types of stapling devices, a drive member moves transversely to the direction the staples are to be driven. Typically, such stapling devices employ a number of staple pusher elements located in grooved slots of a staple cartridge and arranged end to end in rows. During normal operation, the transversely moving drive member contacts a cam member on the staple pusher thereby pushing the staple pusher vertically in the grooved slot. The staple pusher transmits linear motion from the drive member to the staples. The rows of staples are thereby driven into the body tissue to be fastened.

Several issues arise in designing staple pushers for driving one or more surgical staples. If the forces applied to the staple pusher are not effectively balanced, there is a tendency for the staple pusher to twist within the grooved slot and/or bind against the walls of the grooved slot. Additionally, a single point of contact between the actuation sled and the staple pusher may create a rocking point on the staple pusher which can cause the staple pusher to exit the staple cartridge in an unbalanced manner which may result in non-uniform staple formation. Moreover, staple pushers for driving a plurality of staples may offer more resistance to longitudinal movement of the drive member.

It is desirable that the staple pusher permit application of a relatively smooth ejection force throughout the operation of the drive member. It is also desirable that the stapling apparatus form a plurality of finished staples having a substantially uniform configuration. Various staple pusher and cam bar arrangements are known. See, for example, U.S. Pat. Nos. 4,955,959; 4,978,049; 5,395,034; 5,630,541; 5,662,258; 6,131,789; and D278,081.

SUMMARY

The present disclosure is directed towards a staple cartridge. The staple cartridge may include a housing defining a plurality of retention slots for retaining staples. The staple cartridge further includes at least one staple pusher adapted and configured to eject the staples within the retention slots upon actuation of the staple cartridge.

In an embodiment, a staple pusher may include at least two pusher plates including top surfaces that are configured and adapted to engage a staple retained within one of the retention slots. The top surfaces of the pusher plates may be substantially symmetrical, with respect to one another, about a central longitudinal axis of the staple pusher. The pusher plates may be laterally spaced apart, i.e., spaced apart transverse to the central longitudinal axis. In addition, the pusher plates may have substantially equal dimensions and may be substantially positioned along the same points along the central longitudinal axis of the staple cartridge housing. The arrangement of the pusher plates facilitates engagement of staples within retention slots defined within a single column a single column and within separate rows of retention slots.

In an embodiment, the staple cartridge may include a housing defining a first outer row, a second outer row, and at least one inner row of retention slots positioned between the first and second outer rows of retention slots. A staple pusher may include a first and a second pusher plate that are laterally spaced apart to operably engage staples retained in the first and second outer rows of retention slots, and within the same column of retention slots. The lateral spacing of at least some adjacent pusher plates is greater than the lateral spacing of at least some adjacent retention slots. Therefore, the spacing of the pusher plates is such that the pusher plates do not operably engage at least some of the inner rows of retention slots. In addition, the pusher plates may be symmetrically positioned about a central longitudinal axis of the staple pusher.

In an embodiment, the cartridge housing may include three rows of retention slots including two outer rows and one inner row of retention slots. The pusher plates may be configured and adapted to operably engage only the outer rows of retention slots. In particular, the at least one staple pusher may be configured to operably engage at least one staple in each of the first and second outer rows. For example, the at least one staple pusher may include a number of pusher plates, e.g., two pusher plates, that are positioned to operably engage at least one staple in each of the first and second outer rows. In an embodiment, the staple pusher may have no more than two pusher plates. However, in other embodiments, the staple pusher may include a greater or fewer number of pusher plates.

In an embodiment, the staple cartridge includes a housing that defines a longitudinal axis, and an actuation sled that is disposed in the housing. The staple cartridge also includes a plurality of staple pushers including at least one staple pusher that has first and second pusher plates that are laterally spaced apart and symmetrically positioned about the longitudinal axis of the housing. The first plate may have a first plane defined by a first top surface and the second plate has a second plane defined by a second top surface in which the first plane is parallel to the second plane. The staple pusher may include first and second pusher plates that are symmetrically positioned about the longitudinal axis and at the distal end of the housing. The staple pusher may be positioned adjacent to a second staple pusher that includes two pusher plates that are longitudinally and laterally spaced apart from one another.

A staple pusher may be configured to operably engage a plurality of rows of retention slots defined by a housing of a cartridge. The retention slots include at least one or more inner rows such that the staple pusher does not operably engage at least one of the inner rows. The housing may include a plurality of rows of retention slots including at least one or more inner rows, and the at least one staple pusher is configured such that the at least one staple pusher does not operably engage at least one of the inner rows. In addition, at least some of the retention slots may be arranged in columns. The staple pusher may be configured and adapted to operably engage staples within different rows of retention slots, but within the same column of retention slots.

For example, the housing may include three rows of retention slots including two outer retention slots and one inner retention slot. The first and second pusher plates may be configured and adapted to operably engage the outer retention slots and not the inner retention slot. In staple cartridges having more than three rows of retention slots, the staple pusher may be configured and adapted to have pusher plates that only operably engage the outer rows of retention slots.

An actuation sled disposed within the cartridge may be configured to interact with the at least one staple pusher. The actuation sled may include at least one camming member, the at least one camming member including first and second cam wedges that are spaced apart. Each cam wedge includes at least first and second drive faces that are configured to define first and second drive angles with respect to the base of the actuation sled.

An example of a staple cartridge including an actuation sled and at least one staple pusher is found in U.S. Patent Publication 2008/0023522, filed Aug. 30, 2007, the entire contents of which is hereby incorporated by reference.

The various aspects of the present disclosure will be more readily understood from the following description when read in conjunction with the appended figures.

BRIEF DESCRIPTION OF THE DRAWINGS

Embodiments of the disclosure will be described with reference to the accompanying drawings in which:

FIG. 2 is a front perspective view of an actuation sled;

FIG. 3 is a rear perspective view of the actuation sled of FIG. 2;

FIG. 4 is a top plan view of the actuation sled of FIG. 2;

FIG. 5 is a side cross-sectional view of the actuation sled of FIG. 2 taken along section line 5-5 of FIG. 4;

FIG. 6 is a side cross-sectional view of the actuation sled of FIG. 2 taken along section line 6-6 of FIG. 4;

FIG. 9 is a front perspective view of the staple pusher of FIG. 7;

FIG. 10 is a rear perspective view of the staple pusher of FIG. 7;

FIG. 11 is a top plan view of the staple pusher of FIG. 7;

FIG. 12 is a side cross-sectional view taken along section line 12-12 of FIG. 11;

FIG. 13 is a side cross-sectional view taken along section line 13-13 of FIG. 11;

FIG. 16 is a rear perspective view of another embodiment of a staple pusher in accordance with the present disclosure;

FIG. 17 is a top plan view of the staple pusher of FIG. 16;

DETAILED DESCRIPTION

Particular embodiments of the present disclosure will be described herein with reference to the accompanying figures. In the following description, well known functions or constructions are not described in detail to avoid obscuring the present disclosure in unnecessary detail. As shown in the figures and as described throughout the following descriptions, and as is traditional when referring to relative positioning on an object, the term "proximal" refers to the end of the device that is closer to the user and the term "distal" refers to the end of the device that is farther from the user.

Figure 1:
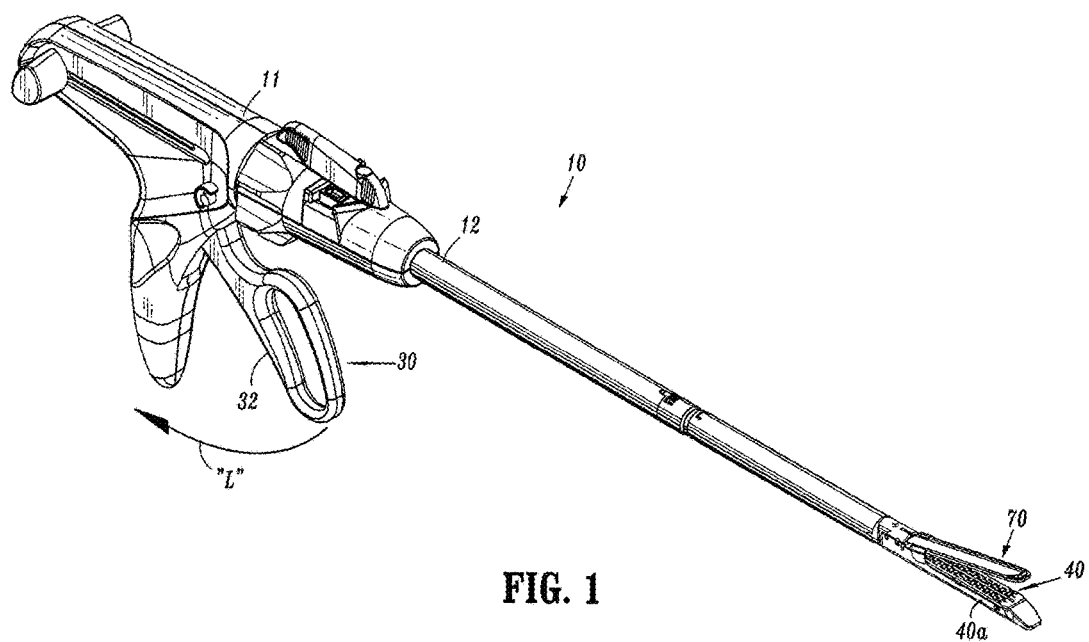
FIG. 1 is a perspective view of an endoscopic surgical stapling device including a staple cartridge.

A surgical stapler 10 will now be described with reference to FIGS. 1-19. Surgical stapler 10, as shown in FIG. 1, includes a housing 11, a trigger assembly 30 pivotably coupled to the housing 11, a body portion 12 extending from the housing 11, a staple cartridge 40, and an anvil assembly 70. An example of a surgical stapler having linear rows is disclosed in U.S. Pat. No. 6,669,073 to Milliman et al., which is currently owned and assigned to United States Surgical, the entire contents of which are incorporated herein by reference.

The trigger assembly 30 includes a trigger 32. Pivotal movement of trigger 32 along directional arrow "L", during an actuation sequence, moves the anvil assembly 70 and the staple cartridge 40 closer relative to each other. By moving the anvil assembly 70 and the staple cartridge 40 closer relative to each other, a portion of body tissue positioned between the anvil assembly 70 and the staple cartridge 40 may be grasped or retained between therebetween.

Figure 7:
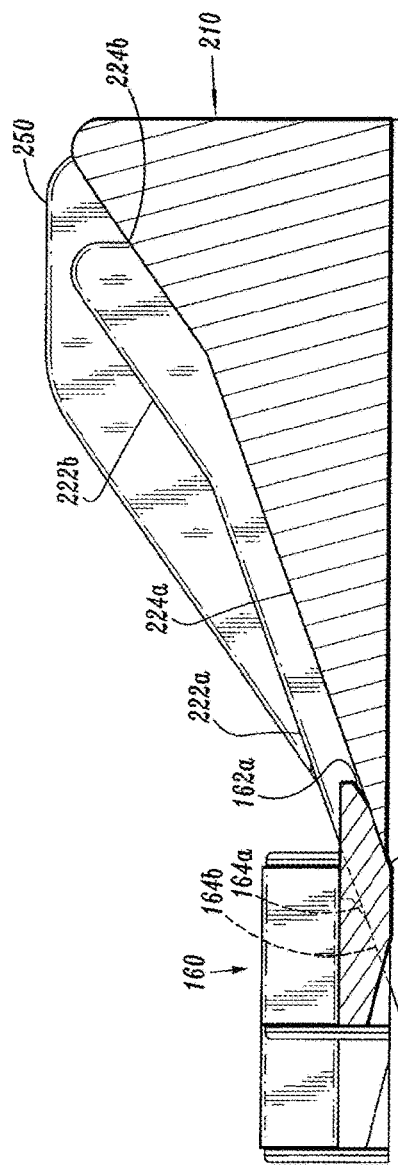
FIG. 7 is a side cross-sectional view of a staple drive assembly including the actuation sled of FIG. 2 showing the initial engagement between the cam members of a staple pusher and the cam wedges of the actuation sled as the actuation sled moves in the direction of arrow "A"
Figure 8:
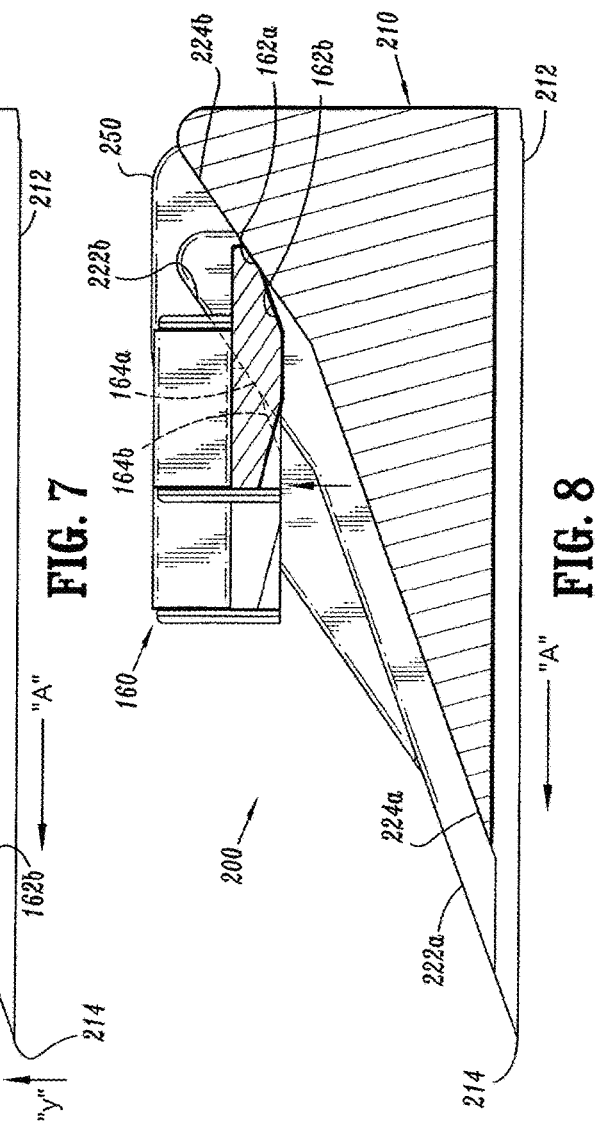
FIG. 8 is a side cross-sectional view of the staple drive assembly of FIG. 7 showing the continued engagement between the cam members of the staple pusher of FIG. 7 and the cam wedges of the actuation sled as the actuation sled continues to move in the direction of arrow "A"

Moreover, actuation of the trigger 32 converts pivotal movement of the trigger 32 into linear movement of a drive mechanism, such as that seen in FIGS. 7 and 8. As an actuation sled 210 (FIGS. 2-8, 16) translates linearly through staple cartridge 40, staple pushers 1260 (FIGS. 14-15; 19), 360 (FIGS. 16, 17, 19), 160 (FIGS. 7-13, 19) interact with the actuation sled 210 to discharge staples 50 (FIG. 18) through retention slots 60. The staples 50 are driven through the portion of body tissue, positioned between the anvil assembly 70 and the staple cartridge 40, in the direction of the anvil assembly 70 to form completed staples.

Figure 18:
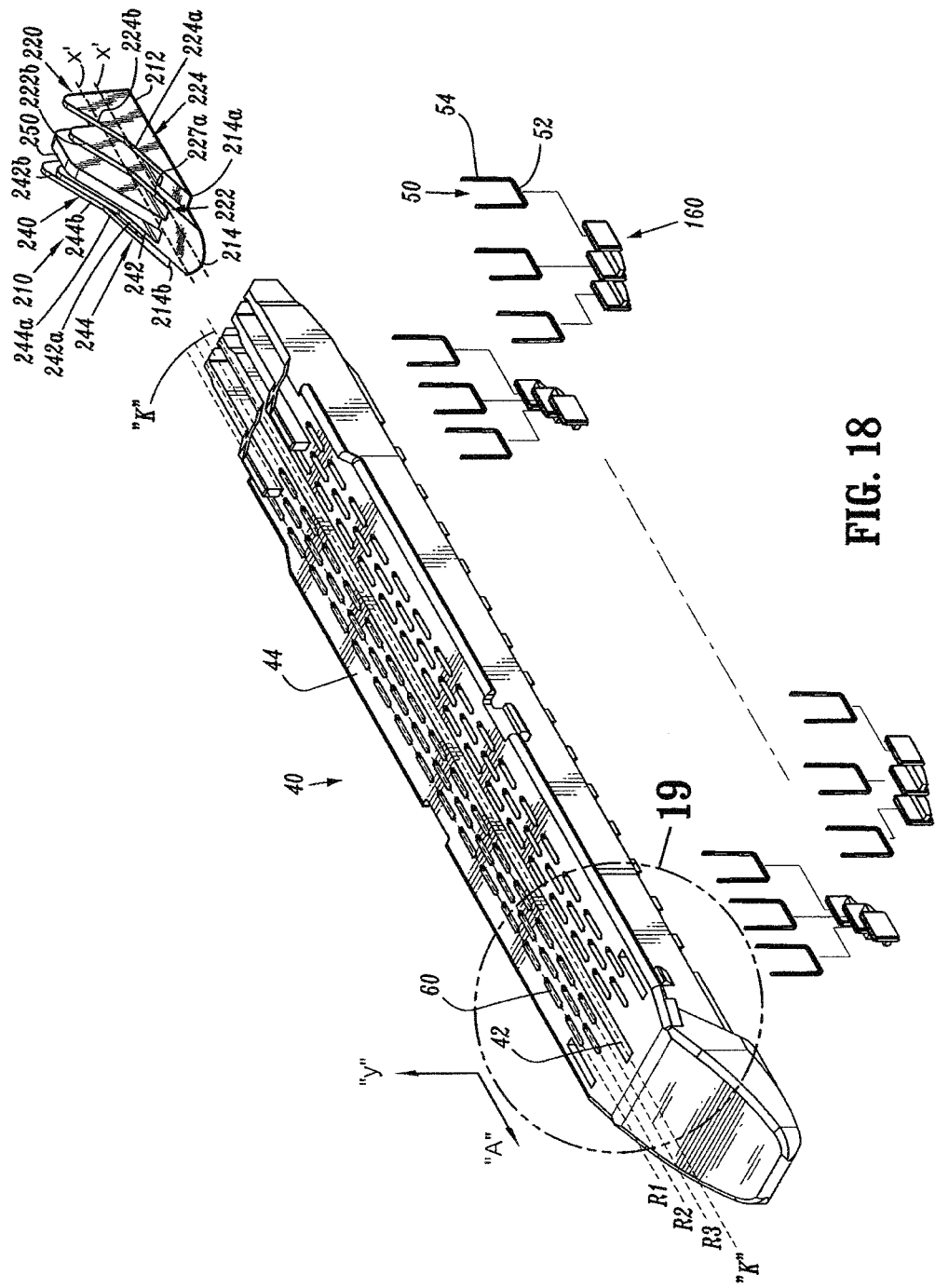
FIG. 18 is an exploded view of the staple cartridge of FIG. 1, staples, staple pushers, and the actuation sled of FIG. 2.

Referring now to FIG. 18, the retention slots 60 are arranged in a plurality of rows R1, R2, R3. Although, three rows are depicted in FIG. 18, the cartridge 40 may include a greater or fewer number of rows. Each of the rows R1, R2, R3 includes retention slots 60 that are coaxial with respect to one another. Moreover, the retention slots 60 may be arranged in columns in which one or more retention slots 60 are positioned along a common axis which is transverse with respect to longitudinal axis "K" of the cartridge 40. As shown in FIG. 18, some columns include two retention slots 60, while others include one retention slot 60 that are symmetrically disposed about longitudinal axis "K".

As seen in FIGS. 2-6, actuation sled 210 is adapted and configured for use in the staple cartridge 40 and includes a first set of camming members 220, a second set of camming members 240, and a guide member 250. Guide member translates along longitudinal axis "K" (FIG. 18) of staple cartridge 40. First and second sets of camming members 220, 240 include respective first or leading cam wedges 222, 242 and respective second or trailing cam wedges 224, 244.

Leading cam wedges 222, 242 of actuation sled 210 include first drive faces 222a, 242a and second drive faces 222b, 242b. Interposed between first drive faces 222a, 242a and second drive faces 222b, 242b are respective first and second transition points 223, 225. First drive faces 222a, 242a extend proximally from a distal point 214 both longitudinally and vertically thereby forming a first drive angle with respect to base 212.

Trailing cam wedges 224, 244 are longitudinally spaced apart from leading cam wedges 222, 242 by a predetermined distance. First drive faces 224a, 244a of trailing cam wedges 224, 244 extend both longitudinally and vertically in a proximal direction from respective origin points 214a, 214b to form the first drive angle with respect to base 212. Second drive faces 222b, 242b form respective second drive angles with respect to plane X' and base 212, which is parallel to plane X'.

Additionally, plane X' extends through transition points 223, 225 (FIG. 6) of trailing cam wedges 224, 244 and is substantially parallel to base 212. Plane X' is also substantially parallel to tissue contacting surface 44 of staple cartridge 40. Second drive faces 224b, 244b form respective second drive angles with respect to plane X'. In one embodiment, first drive angles may be in a range of about 5° to about 35° while second drive angles may be in a range of about 20° to about 55°. In another embodiment, first drive angles may be in a range of about 10° to about 30° while second drive angles may be in a range of about 25° to about 45°. In a further embodiment, first drive angles may be in a range of about 15° to about 25° while the second drive angles may be in a range of about 30° to about 40°.

By providing actuation sled 210 with first drive faces 222a, 242a having a flatter initial engaging surface having a lower angle relative to a plane parallel to base 212, interaction between actuation sled 210 and each staple pusher 160 is more controllable. The interaction between actuation sled 210 and a staple pusher 160 will now be described with reference to FIGS. 7, 8, and 16.

As shown in FIG. 18, actuation sled 210 is configured and adapted to move distally through staple cartridge 40 in a generally horizontal direction as indicated by arrow "A". As actuation sled 210 translates, first drive faces 222a, 224a contact respective second cam surfaces 162b, 164b and urge staple pusher 160 in a generally vertical direction as indicated by arrow "Y" from its first or rest position. As actuation sled 210 translates through staple cartridge 40 and interacts with each staple pusher as discussed above, actuation sled 210 gradually and controllably urges each staple pusher 160 vertically as actuation sled 210 translates through staple cartridge 40. Since the first drive angle is defined by first drive faces 222a, 224a and is complementary to the second receiving angle defined by second cam surfaces 162b, 164b, horizontal movement of actuation sled 210 in direction "A" causes vertical movement of staple pusher 160 in direction "Y".

As shown in FIGS. 7 and 8, as actuation sled 210 continues to move in the direction of arrow "A", second drive faces 222b, 224b engage respective first cam surfaces 162a, 164a and first drive faces 222a, 224a remain engaged with their respective second cam surfaces 162b, 164b, thereby providing additionally longitudinal and vertical stability of staple pusher 160. After actuation sled 210 moves a predetermined distance in the direction of arrow "A", first drive faces 222a, 224a disengage from their respective second cam surfaces 162b, 164b while second drive faces 222b, 224b remain engaged with their respective first cam surfaces 162a, 164a. The second drive angle defined by second drive faces 222b, 224b is complementary to the first receiving angle defined by first cam surfaces 162a, 164a further urging staple pusher 160 in the direction of arrow "Y" through an intermediate position. Continuing distal movement of actuation sled 210 continues to urge staple pusher 160 vertically to its second or end position immediately prior to the disengagement between second drive faces 222b, 224b and respective second cam surfaces 162a, 164a.

Turning now to FIGS. 9-13, several views of staple pusher 160 are illustrated. Each staple pusher 160 includes a first cam member 162, a second cam member 164, and pusher plates 166x, 166y, 166z. In an embodiment, the first can member 162 is positioned between adjacent pusher plates 166x, 166y, and second cam member 164 is positioned between adjacent pusher plates 166y, 166z. In one embodiment, each staple pusher 160 includes three pusher plates 166 that are laterally and longitudinally spaced apart from each other. Generally, first and second cam members 162, 164 and pusher plates 166x, 166y, 166z lie in a plane parallel to a longitudinal axis of staple cartridge 40. Each staple pusher 160 includes a plurality of pusher plates 166 that are substantially parallel to a longitudinal axis of staple cartridge 40, e.g., axis "K" (FIG. 18) and parallel to a centerline CL of each staple pusher (FIG. 11).

Additionally, first and second cam members 162, 164 are also substantially parallel to centerline CL (FIG. 11). Staple pusher 160, as viewed from left to right in FIG. 11, i.e., distal to proximal, includes pusher plate 166x that is laterally spaced apart in the transverse direction from pusher plate 166y. The pusher plate 166x is axially offset from pusher plate 166y in the distal direction. The pusher plate 166y is laterally spaced apart in the transverse direction from pusher plate 166z. The pusher plate 166y is also axially offset from the pusher plate 166z in the distal direction.

Further still, first cam member 162 is disposed between pusher plate 166x and pusher plate 166y. The second cam member 164 is disposed between pusher plate 166y and pusher plate 166z. Each of the pusher plates 166x, 166y, 166z includes a leading edge 166a and a trailing edge 166b. In an embodiment, pusher plates 166x, 166y, 166z may be longitudinally spaced apart or staggered such that the longitudinal spacing between leading edges 166a of adjacent pusher plates 166x, 166y, 166z is about two-thirds the length of retention slot 60 or about two-thirds the length of an adjacent pusher plate 166x, 166y, 166z. Configured thusly, staple pusher 160 has an arrangement where pusher plates 166 are longitudinally staggered from a distal portion of staple pusher 160 to a proximal portion of staple pusher 160 as seen in FIG. 11. Further still, each pusher plate 166x, 166y, 166z includes a top surface 166c that is adapted for releasably engaging a backspan 52 of staple 50.

First and second cam members 162, 164 include respective first and second cam surfaces 162a, 162b and 164a, 164b (FIGS. 9 and 10). At the intersection of first and second cam surfaces 162a, 162b and 164a, 164b are respective transition points 162c, 164c. A plane T (FIGS. 12, 13) extending through transition points 162c, 164c is parallel to respective tops 163, 165 of cam members 162, 164. In one embodiment, first cam surfaces 162a, 164a define a first engagement or receiving angle with respect to tops 163, 165 of respective first and second cam members 162, 164. Second cam surfaces 162b, 164b define a second engagement or receiving angle with respect to plane T. First and second receiving angles are complementary to respective first and second drive angles of camming members 220, 240 of actuation sled 210 as discussed in detail hereinbelow. The receiving angles of the cam members 162, 164 correspond to the drive angles of actuation sled 210.

Figure 14:
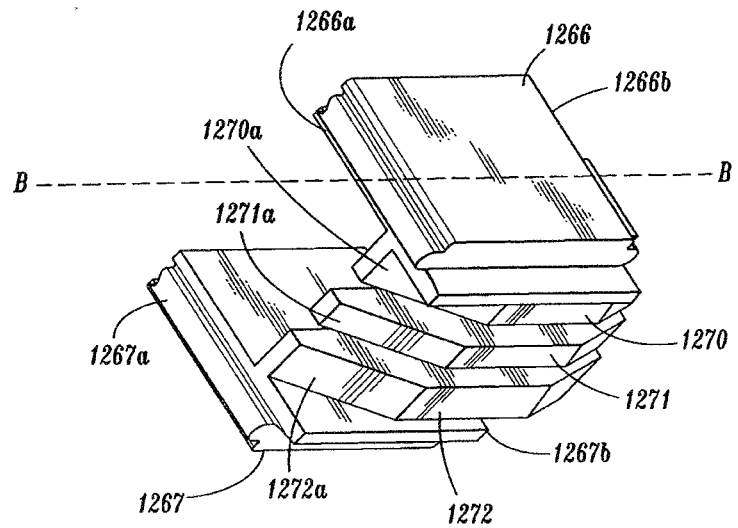
FIG. 14 is a bottom perspective view of a staple pusher according to an embodiment of the present disclosure.
Figure 15:
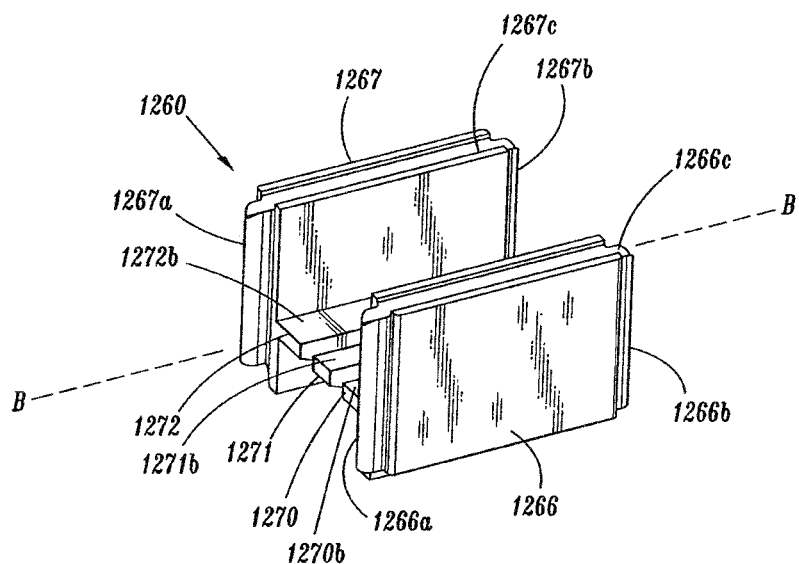
FIG. 15 is a side perspective view of the staple pusher of FIG. 14.

An alternate embodiment of a staple pusher will now be described with reference to FIGS. 14 and 15. Staple pusher 1260, shown in FIGS. 14 and 15, includes a first pusher plate 1266 and a second pusher plate 1267. Pusher plates 1266, 1267 are laterally spaced apart and are symmetrically positioned about a longitudinal axis of housing 40a (FIGS. 1 and 19) of the staple cartridge 40, i.e., axis B positioned between pusher plates 1266, 1267 where pusher plates 1266, 1267 are disposed in respective retention slots 60 of the staple cartridge 40. Staple pusher 1260 is configured and adapted such that pusher plates 1266, 1267 engage outer rows R1, R3, and do not engage inner row R2 of staple cartridge 40 (FIG. 18). It is envisioned that the spacing between pusher plates 1266, 1267 may be adapted such that pusher plates 1266, 1267, of staple pusher 1260, only engage the outer rows of retention slots in staplers having three or more linear rows of retention slots. In an embodiment, staple pusher 1260 may be positioned at either the proximal or distal end of housing 40a of staple cartridge 40. In alternate embodiments, the staple pusher 1260 may be positioned between the proximal and distal ends of the housing 40a.

Each pusher plate 1266, 1267 includes a top surface 1266c, 1267c, respectively, that is adapted for releasably engaging backspan 52 of staple 50. Pusher plate 1266 includes a leading edge 1266a and a trailing edge 1266b. Pusher plate 1267 includes a leading edge 1267a and a trailing edge 1267b. In addition, the staple pusher 1260 includes a first cam member 1270, a second cam member 1271, and a third cam member 1272. Cam members 1270, 1271, 1272 are longitudinally spaced apart and are disposed between pusher plates 1266, 1267. Cam members 1270, 1271, 1272 include respective cam surfaces 1270a, 1271a, 1272a. In an embodiment, cam surfaces 1270a, 1271a, 1272a define engagement or receiving angles with respect to tops 1270b, 1271b, 1272b of respective cam members 1270, 1271, 1272.

The interaction between actuation sled 210 and staple pusher 1260 is substantially similar to that described above with respect to staple pusher 160 with reference to FIGS. 7 and 8 and will therefore not be described in detail. In particular, the receiving angles of the first, second, and third cam surfaces 1270a, 1271a, 1272a of staple pusher 1260 are complementary to the drive angles of actuation sled 210 such that as actuation sled 210 translates distally through staple cartridge 40 in the direction indication by arrow "A" (FIG. 18), sets of camming members 220, 240 of actuation sled 220 slidably engage staple pusher 1260, thereby urging staple pusher 1260 from its first or rest position in a generally vertical direction as indicated by directional arrow "Y" (FIG. 18). The movement of staple pusher 1260 results in top surfaces 1266c, 1267c of the staple pusher 1260 engaging backspan 52 of staple 50 and urging staple 50 in a substantially vertical direction to engage tissue in contact with tissue contacting surface 44 in the direction of anvil 70 to form a completed staple. The interaction between the sets of camming members 220, 240 and staple pusher 1260 is substantially similar to that described between the sets of camming members 220, 240 and staple pusher 160 and that described between the camming members and staple pusher disclosed in U.S. Pat. Pub. 2008/0023522, filed Aug. 30, 2007, the entire contents of which is hereby incorporated by reference.

Figure 19:
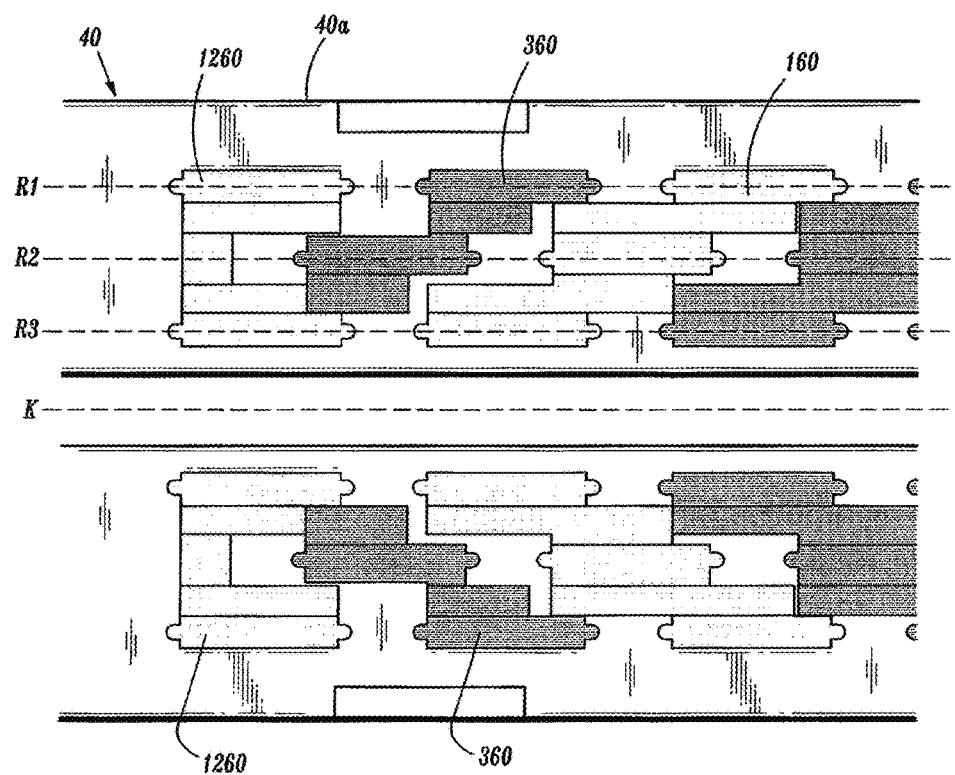
FIG. 19 is an enlarged top view of the indicated area of FIG. 18 depicting staple pushers disposed within the staple cartridge of FIG. 1.

Staple pusher 360 will now be described with reference to FIGS. 16, 17, and 19. As seen in FIG. 19, staple pusher 360 is positioned adjacent and proximal to staple pusher 1260 (FIG. 19). Staple pusher 360 includes a first cam member 362, a second cam member 364, and two prongs or pusher plates 366x, 366y that are laterally and longitudinally spaced apart form each other. Generally, first and second cam members 362, 364 and pusher plates 366x, 366y lie in a plane parallel to longitudinal axis "K" of staple cartridge 40. As illustrated in FIGS. 16 and 17, each pusher plate 366x, 366y includes a leading edge 366a and a trailing edge 366b. Pusher plates 366 may be longitudinally spaced apart or staggered such that the longitudinal spacing between leading edges 366a of adjacent pusher plates 366 is about two-thirds the length of retention slot 60 or about two-thirds the length of pusher plate 366. Further still, each pusher plate 366 includes a top surface 366c that is adapted for releasably engaging a backspan 52 of a staple 50 (FIG. 18). Each retention slot 60 of staple cartridge 40 is configured for releasably receiving a staple 50 and a pusher plate 366.

As shown in FIG. 16, a cam member 362 includes cam surfaces 362a, 362b, and another cam member 364 includes cam surfaces 364a, 364b. At the intersection of first and second cam surfaces 352a, 262b and 364a, 364b are respective transition points 362c, 364c. A plane T (FIG. 16) extending through transition points 362c, 364c is parallel to respective tops 363, 365. In one embodiment, first cam surfaces 362a, 364a define a first engagement or receiving angle with respect to tops 363, 365 of respective first and second cam members 362, 364. Second cam surfaces 362b, 364b define a second engagement or receiving angle with respect to plane T. First and second receiving angles are complementary to respective first and second drive angles of camming members 220, 240 of actuation sled 210.

Additionally, while the present disclosure describes embodiments involving an actuation sled, it will be understood that the design characteristics and function of the sled camming members may be incorporated directly into cam bars or firing wedges, which in turn are connected to the firing mechanism of the surgical stapling instrument.

Furthermore, although the illustrative embodiments of the present disclosure have been described herein with reference to the accompanying drawings, the above description and appended figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. A method of firing surgical staples, comprising:
   advancing staple pushers that are slidably disposed within a staple cartridge, the staple cartridge including staples;
   contacting a first staple and a second staple with corresponding first and second pusher plates of a first staple pusher, the first and second staples being longitudinally aligned and laterally spaced apart;
   contacting a third staple with a first pusher plate of a second staple pusher, the third staple being longitudinally offset from the first and second staples and interposed therebetween;

contacting a fourth staple with a second pusher plate of the second staple pusher; and contacting a fifth staple with a first pusher plate of a third staple pusher, wherein the fourth and fifth staples are longitudinally offset from the first, second, and third staples and laterally aligned with the first and second staples.

2. The method according to claim 1, wherein advancing the staple pushers includes advancing the staple pushers within retention slots defined within the staple cartridge and arranged in first, second, and third rows, wherein the first, second, and third rows are longitudinally aligned and laterally spaced apart such that the second row is interposed between the first and third rows.

3. The method according to claim 2, wherein contacting the first staple and the second staple includes the first and second pusher plates of the first staple pusher being aligned with the first and third rows, respectively.

4. The method according to claim 3, wherein contacting the third staple includes the first pusher plate of the second staple pusher being aligned with the second row.

5. The method according to claim 4, wherein contacting the fourth and fifth staples includes the second pusher plate of the second staple pusher being aligned with the first row and the first pusher plate of the third staple pusher being aligned with the third row.

6. The method according to claim 4, wherein contacting the fourth and fifth staples includes the second pusher plate of the second staple pusher being aligned with the third row and the first pusher plate of the third staple pusher being aligned with the first row.

7. The method according to claim 1, further including advancing an actuation sled within the cartridge assembly.

8. The method according to claim 7, wherein contacting the first staple and the second staple includes advancing the actuation sled such that a portion of the actuation sled abuts the first staple pusher and cams the first and second pusher plates of the first staple pusher into engagement with the first and second staples, respectively.

9. The method according to claim 7, wherein contacting the third staple includes advancing the actuation sled such that a portion of the actuation sled abuts the second pusher and cams the first pusher plate of the second pusher into engagement with the third staple.

10. The method according to claim 7, wherein contacting the fourth staple includes advancing the actuation sled such that a portion of the actuation sled abuts the second staple pusher and cams the second pusher plate of the second staple pusher into engagement with the fourth staple.

11. The method according to claim 7, wherein contacting the fifth staple includes advancing the actuation sled such that a portion of the actuation sled abuts the third staple pusher and cams the first pusher plate of the third staple pusher into engagement with the fifth staple.

12. The method according to claim 1, wherein contacting the staples includes releasably engaging the staples with a respective top surface of the pusher plates.

* * * * *